United States Patent [19]
Sutton

[11] Patent Number: 5,704,926
[45] Date of Patent: Jan. 6, 1998

[54] FLEXIBLE CATHETER

[75] Inventor: Gregg S. Sutton, Plymouth, Minn.

[73] Assignee: Navarre Biomedical, Ltd., Plymouth, Minn.

[21] Appl. No.: 701,569

[22] Filed: Aug. 22, 1996

Related U.S. Application Data

[63] Continuation of Ser. No. 564,984, Nov. 30, 1995, abandoned, which is a continuation of Ser. No. 344,821, Nov. 23, 1994, abandoned.

[51] Int. Cl.$^6$ .................................................. A61M 25/00
[52] U.S. Cl. ........................... 604/282; 604/264; 604/280
[58] Field of Search .............................. 604/95, 282, 264, 604/270, 280, 281

[56] References Cited

U.S. PATENT DOCUMENTS

| | | | |
|---|---|---|---|
| 1,667,443 | 4/1928 | Simonsen | 604/264 |
| 2,269,823 | 1/1942 | Kreiselman . | |
| 3,521,620 | 7/1970 | Cook | 604/95 |
| 4,456,017 | 6/1984 | Miles . | |
| 4,464,176 | 8/1984 | Wijayarathna . | |
| 4,596,563 | 6/1986 | Pande . | |
| 4,639,252 | 1/1987 | Kelly et al. | 604/282 |
| 4,655,746 | 4/1987 | Daniels et al. . | |
| 4,739,768 | 4/1988 | Engelson . | |
| 4,748,979 | 6/1988 | Hershenson . | |
| 4,798,598 | 1/1989 | Bonello et al. | 604/95 X |
| 4,813,434 | 3/1989 | Buchbinder et al. | 604/95 X |
| 4,813,934 | 3/1989 | Engelson et al. . | |
| 4,838,268 | 6/1989 | Keith et al. . | |
| 4,842,590 | 6/1989 | Tanabe et al. . | |
| 4,884,579 | 12/1989 | Engelson . | |
| 4,917,666 | 4/1990 | Solar et al. | 604/96 X |
| 4,955,862 | 9/1990 | Sepetka . | |
| 4,976,690 | 12/1990 | Solar et al. . | |
| 4,985,022 | 1/1991 | Fearnot et al. | 604/282 |
| 4,994,069 | 2/1991 | Ritchart et al. . | |
| 5,045,072 | 9/1991 | Castillo et al. . | |
| 5,047,045 | 9/1991 | Arney et al. . | |
| 5,095,915 | 3/1992 | Engelson . | |
| 5,135,494 | 8/1992 | Engelson et al. . | |
| 5,147,317 | 9/1992 | Shank et al. | 604/282 X |
| 5,171,232 | 12/1992 | Castillo et al. . | |
| 5,178,158 | 1/1993 | de Toledo | 604/282 X |
| 5,195,989 | 3/1993 | Euteneuer . | |
| 5,228,453 | 7/1993 | Sepetka . | |
| 5,243,988 | 9/1993 | Sieben et al. . | |
| 5,308,324 | 5/1994 | Hammerslag et al. | 604/95 |
| 5,334,169 | 8/1994 | Brown et al. | 604/280 |
| 5,378,234 | 1/1995 | Hammerslag et al. | 604/95 |
| 5,395,332 | 3/1995 | Ressemann et al. | 604/280 X |

OTHER PUBLICATIONS

"Care and Maintenance of Cardiac Catheters," brochure entitled *U.S.C.I. Cardiac Catheters and Electrodes* United States Catheter & Instrument Corporation, Glens Fall, New York, copyright 1961, three sheets.

Product sheet entitled "*Catheters for Cardiology,*" United States Catheter & Instrument Corp., Glens Falls, New York, 1963 two sheets.

(List continued on next page.)

*Primary Examiner*—Michael Powell Buiz
*Assistant Examiner*—N. Kent Gring
*Attorney, Agent, or Firm*—Gregory P. Kaihoi

[57] ABSTRACT

The invention provides a catheter capable of delivering drugs or other fluids to a desired remote location in a bodily passageway, such as a small, tortuous artery. The catheter of the invention includes inner and outer tubular layers, and a continuous helical wire coil disposed between the tubular layers along substantially the entire length of the catheter. To enhance trackability and pushability, the wire coil is constructed to provide regions of differing flexibility to the catheter. The wire coil in a first portion of the catheter has a first coil pitch and the wire coil in a second section of the catheter has a second coil pitch which is larger than the first coil pitch to provide the second section of the catheter with greater flexibility than the first section.

20 Claims, 2 Drawing Sheets

OTHER PUBLICATIONS

Product brochure entitled *"Cardiology Radiology Surgery, Cardiovascular Catheters and Accessories,"* United States Catheter & Instrument Corp., 1967,68, five sheets.

Product brochure entitled *"Cardiovascular Catheters and Accessories—Cardiology Radiology Surgery,"* United States Catheter and Instrument Corporation, Glens Falls, New York, 1969, six sheets.

Product brochure entitled "Cardiovascular Catheters and Accessories—Woven Dacron, Teflon and Polyethylene Materials," USCI, a Division of C.R. Bard, Inc., Billerica, Massachusetts, Jun. 1974, eight sheets.

Product brochure entitled *"Venture into the New Frontier,"* SciMed Life Systems, Inc., Maple Grove, Minnesota, 1993, one sheet.

Brochure entitled "Transit™ Infusion Catheter—Taking the Kinks Out of Interventional Therapy," Cordis Endovascular Systems, Inc., Miami Lakes, Florida, Oct. 1993, two sheets.

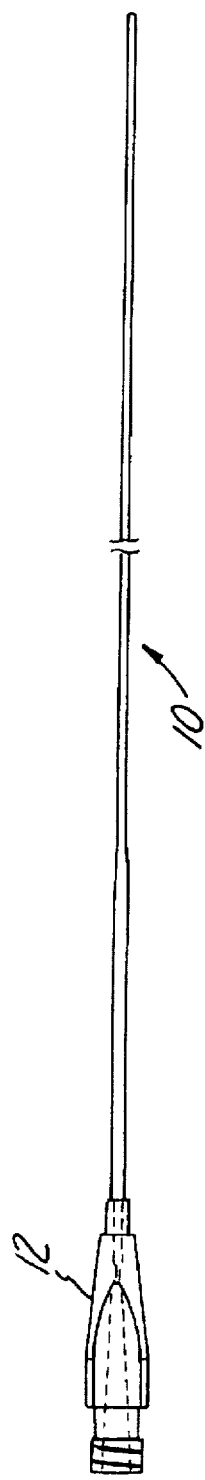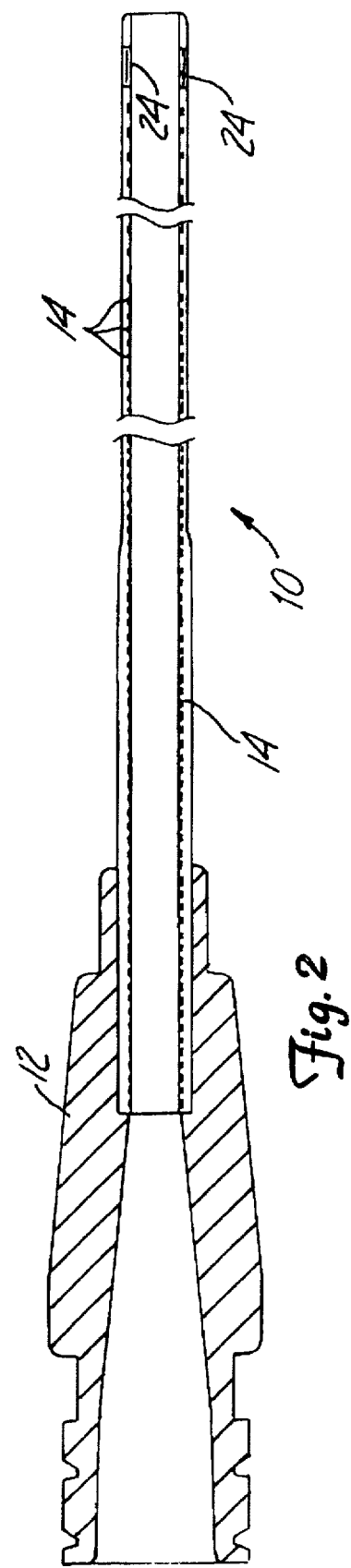

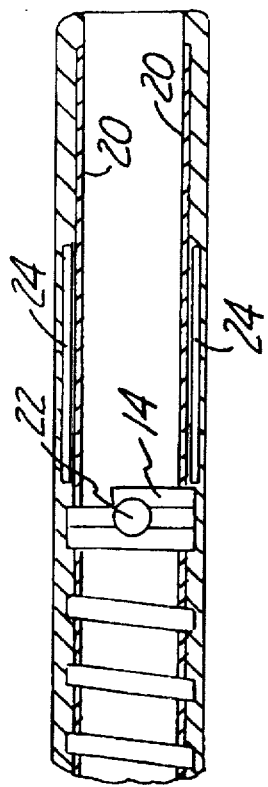
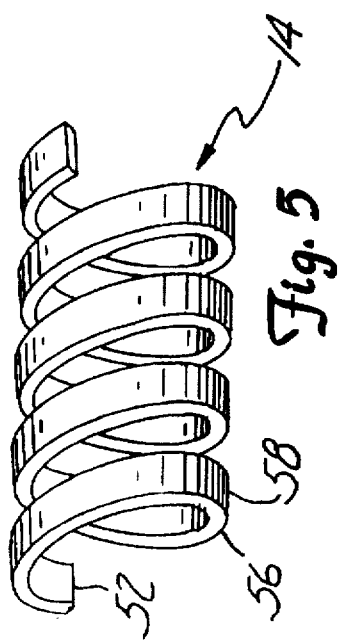
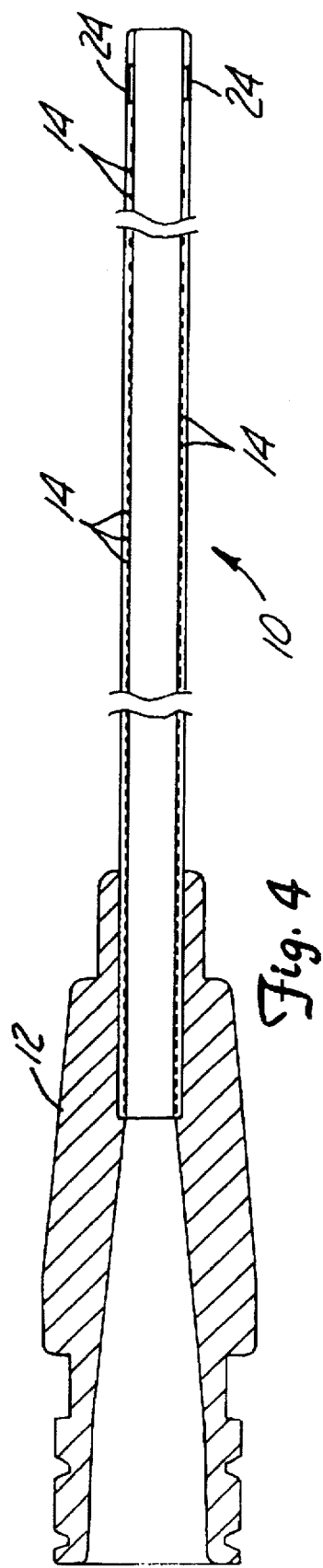

FLEXIBLE CATHETER

This application is a continuation of application Ser. No. 08/564,984, filed Nov. 30, 1995 now abandoned, which is a continuation of application Ser. No. 08/344,821, filed Nov. 23, 1994 now abandoned.

FIELD OF THE INVENTION

This invention relates to catheters used in medical procedures.

BACKGROUND OF THE INVENTION

Catheters find a variety of applications in medical procedures for providing access to selected locations within a bodily passageway or cavity. A particularly common application of catheters is for intravascular access for the administration of drugs, fluids or occlusive devices. Infusion catheters typically are introduced in combination with a guiding catheter and a guide wire.

Infusion catheters are typically placed percutaneously via the femoral artery, although other arterial or venous entries are also used. Infusion catheters have many applications in the peripheral, coronary and neurovasculature. These include delivery of chemotherapy drugs, delivery of blood thinning agents to break down blood thrombosis, infusion of contrast media for fluoroscopic imaging, or delivery of devices for treating aneurysms and arteriovenous malformations. In all these applications, the ability to access very selective and remote arterial or venous locations is critical.

Important performance characteristics of infusion catheters utilized for these and similar purposes include distal flexibility, pushability over a guide wire, luminal fluid carrying capacity, kink-resistance, frictional characteristics of inner and outer surfaces, and distal tip radiopacity.

Prior art infusion catheters typically consist of tubes made of a polymeric materials, sometimes in combination with metallic reinforcement. Such catheters of the prior art, while providing adequate means to access vascular sites, have distinct disadvantages. Often they are fabricated from polymers which soften somewhat when inserted into a body (due to the effects of temperature). In some applications (such as smaller, more tortuous arteries) it is desirable to construct the catheter from very flexible materials to facilitate advancement of catheters into such difficult access locations. As a result, however, such catheters can become more difficult to manipulate, have a tendency to kink and buckle, lack axial energy transmission (i.e., poor pushability) and can also tend to bind against the guiding catheter and/or guide wire. Catheter designs intended to minimize such deficiencies often must do so at the expense of flexibility, resulting in poor trackability (i.e., ability of the catheter to follow and conform to the curves of a guide wire without causing the guide wire to straighten out).

Catheters have been made which provide different regions of flexibility - - - i.e., a stiffer proximal section and a more flexible distal section. Examples of such catheters include U.S. Pat. No. 4,464,176, which describes a catheter made of two layers of tubing, one of the layers being more flexible than the other and extending distally beyond the end of the other layer by a considerable distance. U.S. Pat. No. 4,739,768 shows a similar structure, and further suggests the use of three layers of tubing to construct a catheter with three different degrees of flexibility. Utilizing solely the thickness of the catheter wall to control flexibility requires, however, that the stiffer portion of the catheter be necessarily proportionally thicker. Others have addressed this problem by constructing a catheter from two lengths of tubing of dissimilar materials, one being more flexible than the other (see, e.g., U.S. Pat. No. 4,842,590). Such constructions introduce additional manufacturing complexity, however, in joining such lengths in a consistently reliable fashion. Others have utilized dissimilar metal reinforcing materials to achieve differing flexibility - - - e.g., relatively stiffer wire braiding in the proximal portion and a relatively more flexible helical coil in the distal portion. Again, the use of such differing materials requires careful quality control in manufacturing, to assure proper performance at the junction of the dissimilar materials.

There is, therefore, a need for catheters that provide a variable degree of flexibility in a relatively small size (i.e., diameter) to facilitate access to remote locations through sometimes lengthy and tortuous passageways. As the pushability of catheters generally decreases with smaller size and greater flexibility, there is a need for such flexible, small catheters that have excellent pushability and trackability and are without introducing manufacturing complexities.

SUMMARY OF THE INVENTION

The invention provides a catheter capable of delivering drugs or other fluids to a desired remote location in a bodily passageway, such as a small, tortuous artery. The catheter of the invention includes inner and outer tubular layers, and a continuous helical wire coil disposed between the tubular layers along substantially the entire useable length of the catheter. To enhance both trackability and pushability, the wire coil is constructed to provide regions of differing flexibility to the catheter. The wire coil in a first (typically proximal) portion of the catheter has a first coil pitch (i.e., the distance, measured center to center along the length of the catheter, from one turn of the wire coil to the next adjacent turn), and the wire coil in a second (typically distal) section of the catheter has a second coil pitch which is larger than the first coil pitch to provide the second section of the catheter with greater flexibility than the first section. The first, less flexible section therefore typically has greater pushability, and typically comprises a substantial portion of the length of the catheter, with the second, more flexible (and therefore typically less pushable) portion comprising a distal section of at least, e.g., about 5 cm, and preferably about 15–30 cm. Desirably the pitch of the wire coil in the second portion is at least about 25% larger than in the first portion, and preferably at least about 50% larger.

The wire coil preferably terminates very close to the distal end of the catheter, desirably within a distance of not more than about five times the outer diameter of the tubular layers (and preferably not more than the actual diameter of such layers), measured at the distal end of the wire coil. In a preferred embodiment one or both ends of the wire coil are secured by a weld attaching at least two (preferably three) adjacent turns of the coil to one another. A radiopaque marker may be provided, disposed between the tubular layers at the distal end of the catheter (either positioned just distally of the distal end of wire coil, or positioned over this distal end portion of the wire coil). Preferably the wire coil is made from a metal wire having a generally rectangular cross-section. In a preferred embodiment, the width of the wire, in cross-section, is at least twice its thickness. In some applications, the wire coil may include three distinct regions of differing pitch (and therefore flexibility). Also, a third tubular layer may be disposed along a proximal section of the inner and outer tubular layers (desirably between such layers), to provide such proximal section with greater stiffness.

Catheters made in accordance with the invention preferably include an outer layer formed so as to enter into and substantially fill the interstices of the coil, thereby placing the outer layer in intimate contact with the inner layer. This construction gives the catheter structural integrity greater than, for example a catheter made with an outer layer which has merely been shrunk over a reinforcing coil or braid.

BRIEF DESCRIPTION OF THE DRAWINGS

FIG. 1 shows a catheter of the invention;

FIG. 2 shows an enlarged, cross-sectional view of the catheter of FIG. 1;

FIG. 3 shows in further enlarged detail the distal end of a catheter of the invention;

FIG. 4 is a view similar to FIG. 2, depicting an alternate embodiment of the invention; and FIG. 5 is a perspective view of a preferred wire coil utilized in a catheter of the invention.

DESCRIPTION OF THE PREFERRED EMBODIMENT

Referring to FIG. 1, a catheter of the invention is comprised of an elongated tubular member 10, having substantially circular (in cross-section) inside and outside walls which are preferably substantially smooth. The tubular member 10 is secured at its proximal end to a suitable Luer fitting 12. Tubular member 10 is comprised of an encapsulating material and an encapsulated wire coil 14 as shown in FIGS. 2–5. The reinforcement provided by the wire coil enables the catheter to resist kinking and collapse, as well as the ability to better withstand the hoop stresses of any internal pressure. The helically wound wire coil also provides this reinforcement while preserving significant flexibility of the catheter. Moreover, such flexibility can be controlled by varying the pitch of the coil - - - a smaller pitch (i.e., tighter spacing of successive turns of the wire coil) provides relatively less flexibility with greater pushability, while a larger pitch (i.e., wider spacing of successive turns of the wire coil) provides relatively greater flexibility with better trackability, though somewhat less pushability. Although the drawings, which are somewhat schematic, show varying pitches for the wire turns, as described below, preferably the wire coil is wound with a rather tight pitch in the proximal section of the catheter to provide good axial compressive strength (and therefore good pushability). This pitch is desirably no more than about 150% of the cross-sectional width of the wire, and preferably less than about 125% of such cross-sectional width.

The coil pitch in a distal section of the catheter is larger, to provide greater flexibility and trackability to the distal portion of the catheter. Desirably the pitch of the distal section of the wire is between 150% and 300% of the cross-sectional width of the wire. In a particularly preferred embodiment utilizing 0.001×0.003" rectangular wire, the pitch of the wire coil in the proximal section is about 0.0035" and the pitch of the wire coil in the distal section is about 0.007". By using the very same, continuous wire to provide varying flexibility to the catheter, manufacturing and quality control processes are simplified in comparison to other techniques which rely on joining sections of different stiffness materials, such as different stiffness tubing and/or different stiffness metal reinforcing structures.

The encapsulating material may be a single layer of suitable flexible material, but more preferably is multi-layered, as shown in the drawings. The materials of choice include elastomers such as polyurethane or silicone robber. Different materials will result in various levels of flexibility, pushability, trackability and kink resistance. Those skilled in the art will also recognize that when increased torque is applied to the catheter tubing 10 additional reinforcement in the form of multi-wire braiding, multifillar windings and other metallic or nonmetallic reinforcement may be used.

Materials and material types suitable for use as the tubing encapsulating material include:

TABLE A

| MATERIALS | MANUFACTURES (TRADE NAMES) |
|---|---|
| (A) polyesterurethane: | B. F. Goodrich (Estane) |
|  | DuPont (Hytrel) |
| (B) polyetherurethane: | Dow (Pellathane) |
|  | B. F. Goodrich (Estane) |
| (C) aliphatic polyurethane: | Thermedics (Tecoflex) |
| (D) polyimide: | DuPont (Pyraline) |
| (E) polyetherimide: | General Electric (Ultem) |
| (F) polycarbonate: | Mobay (Apec) |
| (G) polysiloxane: | Dow Corning (Silastic) |
|  | Dow Corning (MDX-4159) |
| (H) hydrophilic polyurethane: | Grace Co. (Hypol) |
| (I) polyvinyls: |  |
| (J) latex: |  |
| (K) hydroxy-ethyl methacrylate: |  |
| (L) blends of the above materials: |  |
| (M) other elastomers that can be carried in solvent. |  |

The above-listed materials when used alone or as components in a blend of materials have displayed excellent performance in robing manufactured by Navarre Biomedical Ltd. of Minnesota. The subsequent products produced with these materials allow for a range of performance characteristics. Some of the blends of materials discussed below offer specific performance advantages.

In the present invention these materials have been successfully used to manufacture thin walled encapsulating robe. These materials desirably are prepared with a solvent system manufacturing process according to the following proportions listed in Table B. The materials listed herein are by way of illustration and not by way of limitation. Similar materials known to those skilled in the art having equivalent properties may also be used.

TABLE B

| (A) urethanes: | solids: | 6% to 14% |
|---|---|---|
|  | solvents: | THF/DMF 85/15 (THF - Tetrahydrofuran, DMF -Dimethyl-formamide) |
|  | viscosity: | 10–100 centistokes |
| (B) polyimide: | solids: | 20%–45% |
|  | solvents: | N-Methylpyrrolidone |
|  | viscosity: | 80–1000 centistokes |
| (C) polyetherimide | solids: | 8% to 12% |
|  | solvents: | methylene chloride |
|  | viscosity: | 40–100 centistokes |
| (D) polycarbonate: | solids: | 6% to 12% |
|  | solvents: | THF/DMF 85/15 |
|  | viscosity: | 10–60 centistokes |
| (E) polysiloxane: | solids: | 30%–60% |
|  | solvents: | 111-trichloroethane |
|  | viscosity: | 100–450 centistokes |
| (F) hydrophilic polyurethane: | solids: | .1%–95% |
|  | solvents: | water |
|  | viscosity: | not applicable |

The preparation of the encapsulating materials may be accomplished as follows. The solvent is added to the solid or liquid material in the appropriate mount to make the desired percent solids. Stirring is necessary to completely solvate plastic materials. Once the plastic is completely in solution the material is ready for use in coating applications for making the tubing of the invention. The encapsulating material 22 is configured to substantially cover the reinforcing coil 14.

FIG. 5 shows a schematic isometric drawing of an example of a reinforcing coil 14. The reinforcing coil 14 in the kink resistant tubing apparatus of the invention provides radial strength and hoop strength. The reinforcing coil 14 helps retain the circularity of the tubing 10 and thereby avoids buckling and kinking of the tubing 10. The reinforcing coil 14 also provides a crush-resistance to the reinforcing coil. The reinforcing coil 14 comprises a wire which may have various cross-sectional shapes, such as, for example, rectangular, circular, or elliptical. Those skilled in the art will recognize that the cross-sectional shapes will effect the load bearing characteristics and strength characteristics of the reinforcing coil 14. In the example of FIG. 5 the cross-section 52 is rectangular with a flat face 56 and flat body 58.

Various different reinforcing coil 14 materials may be used. Further, the reinforcing coil dimensions can vary as well as the reinforcing coil 14 pitch and diameter. Listed below in Table C are some of the alternative coil 14 design parameters that can be used.

TABLE C

| | |
|---|---|
| Coil Wire Size: | 0.001–0.015 |
| Coil Wire Material: | metals; stainless steel, MP35, NiTi, Tungsten, Platinum, kevalar, nylon, polyester, acrylic |
| Coil Pitch: | 1–5 times maximum coil wire dimension (preferably 1–2 times such dimension) |
| Coil Diameter: | 0.010–0.375 inches |

A preferred manufacturing method for constructing catheters accordingly to the invention involves four major steps described in detail below: mandrel coating or overextruding, coil wrapping of mandrel substrate, over coating the coiled assembly, and mandrel extraction.

A mandrel is first coated or overextruded with what will become the inner layer 20 (see FIG. 3) of the catheter. The mandrel provides the internal dimensions of the catheter, and may be advantageously constructed from a fluoropolymer such as PTFE or FEP, polyethylene, nylon, or possibly a ductile metal such as silver, copper or nickel. The mandrel may be tubular or solid and may advantageously be diametrically reduced upon the application of sufficient stretching force. If a tubing is used for the mandrel, a support rod, usually metallic, can be used to provide increased straightness and stiffness.

The mandrel may be coated with a thin layer or layers of a first encapsulating material (preferably PTFE or a similar low friction material) in solution form, using, e.g., the solution draw process described below. This can require one to several coats depending on tubing specifications and encapsulating material viscosity. Typically inner layers are coated to thicknesses of about 0.0005–0.005 inches. Solution draw rates of, e.g., 6–18 inches per minute can be used to apply the inner layer of encapsulating material. As indicated above, the mandrel may alternately be overextruded with the inner layer of thermoplastic material, using well-known thermoplastic extrusion techniques.

After the inner layer 20 has been applied to the mandrel, the reinforcing coil 14 is wrapped onto this inner layer 20.

The coil wrapping process involves wrapping the reinforcing coil wire 14 at the proper tension and pitch. The coil wire is wrapped around the coated mandrel uniformly to the desired specifications. The coil's material composition, rotational speed, tension, substrate diameter and pitch determine the size and flexibility of the coil. A conventional coil wrapping apparatus may be utilized for this function, such as, for example, an Accuwinder (™) machine as manufactured by the Accuwinder Company of California. The coil wire 14 must be secured to the lead end of the mandrel substrate, as by an adhesive, or by spot welding two or, preferably, three successive turns of the coil together. The substrate is then wrapped from end to end using the predetermined coil wrapping parameters. In particular, the pitch of the coil is changed at the desired location along the length of the mandrel to produce a catheter having the desired flexibility requirements. Once the coil wrap is complete, the distal end of the coil 14 must be secured. This may be accomplished by suitable adhesives, or, preferably by spot welding two or, preferably, three successive turns of the coil together. FIG. 3 illustrates a spot weld 22 securing three adjacent turns of the distal end of the coil 14. After securing the end of the coil, the wire 14 can be cut and the coiled substrate removed from the machinery.

The process variables for the coiling operation include the wire wrapping speed and coil wire tension. Wrapping speeds of between about 500 and 4000 rpm and coil wire tensions of between about 25 and 200 grams have worked well.

After the coil has been suitably wrapped about the coated mandrel, a radiopaque marker 24 may be placed on or near the distal end of the coil, and encapsulating material may then be applied over the entire assembly. The coil 14 is over coated to a predetermined thickness using the solution draw process described below.

The solution draw process is comprised of a number of steps. The first step is to prepare the encapsulating material in a solution form. The mandrel is drawn through the solution of the encapsulating material. The solution is held in a container having a hole slightly larger than the size of the mandrel. The mandrel is then drawn through the solution and the encapsulating material is deposited on the mandrel. The resulting encapsulating material thickness is highly controllable due to the propensity of the encapsulating material to adhere to the mandrel.

After the proper thickness of encapsulating material has been applied, the mandrel and encapsulating material is cured for the appropriate time (determined based on the type of material used).

Exemplary process variables are summarized as follows in Table D.

TABLE D

| Environmental | |
|---|---|
| Ambient temp: | 65° F.–76° F. |
| Humidity: | 10–35% relative |
| Solution Viscosity: | 1–100 centistokes |
| Solution Draw Rate: | 6–10 inches per minute |
| Solvent Evaporation Rate: | 14.5 using N-Butylacetate standard |
| Solution Temp. | 65° F.–76° F. |
| Solution Chemistry | 6%–14% solids (Such as Polyurethane in solution with highly polar solvents.) |

After the coating operation is completed, the mandrel may be suitably extracted, e.g., by securing each exposed termination of the mandrel and applying sufficient and directionally opposite forces to plastically reduce the diameter of the mandrel by 10–50%. Once this is accomplished, the mandrel can simply be removed from the tubing assembly.

In one embodiment (depicted in FIGS. 1–2) the catheter is effectively divided into three segments, a proximal segment having a greater wall thickness, an intermediate segment having a lesser wall thickness but with the same coil pitch as the proximal segment, and a distal segment having the same wall thickness as the intermediate segment but with a larger coil pitch. Each segment of this catheter, therefore has a different flexibility. Alternately, a third degree of flexibility could be provided to a catheter by utilizing three (or more) different pitches in three different segments of the catheter.

Particularly preferred dimensions of catheters constructed in accordance with the invention are in the size range of 2–6 French, utilizing stainless steel wire (with a cross-sectional dimension of about 0.001×0.003" to about 0.002×0.005") wound about an inner layer of PTFE of a thickness of about 0.002–0.003"; an outer encapsulating layer of Estane brand polyesterurethane coated to a thickness of about 0.002–0.004" (preferably no more than about 0.01"); and an outer thin layer of a hydrophilic coating, such as the coatings described in U.S. Pat. No. 4,847,324. Preferably the wire is wound in the proximal section of the catheter with a pitch of less than about 150% of the wire's cross-sectional width, and is wound in the distal section with a pitch of less than about five times its width, and preferably about two to three times its width. Catheters of such construction provide excellent flexibility, pushability, trackability, and have excellent kink-resistance.

While a preferred embodiment of the present invention has been described, it should be understood that various changes, adaptations and modifications may be made therein without departing from the spirit of the invention and the scope of the appended claims.

What is claimed is:

1. A catheter capable of delivering drugs, fluids or occlusive devices to a desired location in a bodily passageway or cavity comprising:

a elongated cannula having proximal and distal ends and inner and outer tubular layers extending along substantially the entire useable length of the elongated cannula;

a proximal fitting secured to the proximal end of the elongated cannula;

a continuous helical wire coil disposed between the tubular layers along substantially the entire useable length of the elongated cannula, the wire coil in a first section of the tubular layers having a first coil pitch, and the wire coil in a second section of the tubular layers having a second coil pitch which is larger than the first coil pitch to provide the second section of the tubular layers with greater flexibility than the first section.

2. The catheter of claim 1 wherein the first section of the tubular layers is a proximal section and the second section of the tubular layers is a distal section.

3. The catheter of claim 1 wherein the wire coil terminates in a distal end, both tubular layers of the catheter extending distally of the wire coil a distance not more than five times the outer diameter of the tubular layers, measured at the distal end of the wire coil.

4. The catheter of claim 3 further including a radiopaque marker disposed between the tubular layers at the distal end of wire coil.

5. The catheter of claim 1, wherein the wire coil is made from a metal wire having a generally rectangular cross-section.

6. The catheter of claim 5 wherein the width of the wire, in cross-section, is at least twice its thickness.

7. The catheter of claim 1 wherein the wire coil in a third section of the tubular layers, intermediate the first and second sections of the tubular layers, has a third coil pitch intermediate the coil pitches of the first and second sections of the tubular layers, providing an intermediate section of the tubular layers with a flexibility intermediate that of the first and second sections of the tubular layers.

8. The catheter of claim 1 further including a third tubular layer disposed between the inner and outer tubular layers along a proximal section of the inner and outer tubular layers, to provide the proximal section with greater stiffness.

9. The catheter of claim 1 wherein the second coil pitch is at least about 25% larger than the first coil pitch.

10. The catheter of claim 1 wherein the second coil pitch is at least about 50% larger than the first coil pitch.

11. The catheter of claim 1 wherein the first coil pitch is less than 150% of the cross-sectional width of the wire, and the second coil pitch is between 150% and 300% of the cross-sectional width of the wire.

12. The catheter of claim 11 wherein the second coil pitch is at least about 25% larger than the first coil pitch.

13. The catheter of claim 11 wherein the second coil pitch is at least about 50% larger than the first coil pitch.

14. The catheter of claim 1 wherein the second section is at least about 5 cm in length.

15. The catheter of claim 1 wherein the second section is at least about 15 cm in length.

16. The catheter of claim 1 wherein at least one end of the helical wire coil is secured by a weld attaching two adjacent turns of the coil to each other.

17. The catheter of claim 16 wherein the weld secures three adjacent turns to one another.

18. The catheter of claim 16 wherein each end of the helical wire coil is secured by such a weld.

19. The catheter of claim 1 wherein spaces between adjacent turns of the wire coil define interstices through which the outer tubular layer contacts the inner tubular layer, thereby enhancing the structural integrity of the catheter.

20. A catheter comprising an elongated tubular member defining a catheter lumen capable of receiving a guide wire therein, and a continuous helical wire coil embedded in the tubular member along substantially the entire useable length thereof, the wire coil in a first section of the tubular member having a first coil pitch, and the wire coil in a second section of the tubular member having a second coil pitch which is at least 25% greater than the first coil pitch to provide the second section of the tubular member with greater flexibility than the first section of the tubular member.

* * * * *